(12) United States Patent
Eisenberg et al.

(10) Patent No.: US 10,613,036 B2
(45) Date of Patent: Apr. 7, 2020

(54) CONVEYING AND CLEANING SYSTEM AND METHODS FOR CLEANING AND STACKING TRAYS AND/OR LAYER PADS

(71) Applicant: United Sortation Solutions, LLC, Owings Mills, MD (US)

(72) Inventors: Howard Eisenberg, Owings Mills, MD (US); Darius Scott, Owings Mills, MD (US)

(73) Assignee: United Sortation Solutions, LLC, Owings Mills, MD (US)

( * ) Notice: Subject to any disclaimer, the term of this patent is extended or adjusted under 35 U.S.C. 154(b) by 497 days.

(21) Appl. No.: 14/879,589

(22) Filed: Oct. 9, 2015

(65) Prior Publication Data
US 2017/0100752 A1 Apr. 13, 2017

(51) Int. Cl.
*A61L 2/07* (2006.01)
*G01N 21/88* (2006.01)
(Continued)

(52) U.S. Cl.
CPC ............ *G01N 21/8851* (2013.01); *A61L 2/07* (2013.01); *B07C 5/342* (2013.01); *B08B 9/0861* (2013.01);
(Continued)

(58) Field of Classification Search
CPC ....... A61L 2/07; A61L 2202/122; B08B 1/02; B08B 3/022; B08B 2230/01; B65G 43/08; B65G 2201/02
(Continued)

(56) References Cited

U.S. PATENT DOCUMENTS

| 2,651,065 A | * | 9/1953 | O'Connor | ............... A47L 15/39 |
| | | | | 15/56 |
| 2,698,627 A | * | 1/1955 | Kearney | ............... A47L 15/247 |
| | | | | 134/111 |

(Continued)

*Primary Examiner* — David G Cormier
*Assistant Examiner* — Thomas Bucci
(74) *Attorney, Agent, or Firm* — Alston & Bird LLP

(57) ABSTRACT

The invention comprises a steam cleaning system that can rapidly handle multiple objects in an efficient and useful way. For example, objects used for shipping or moving food products in the food manufacturing or food services industries must either be new, clean and used once and then discarded, or re-used and thus cleaned to ensure no contamination is present. Layer pad objects or other separating surfaces are often used in these industries and often when these objects are used in stacking and pelletizing large shipments of food products, where the payer pad or other separating or container objects or surfaces help contain or maintain the integrity of the food products during shipment. In an important aspect of the invention, a plastic layer pad cleaning system is described. In other aspects, other surfaces, containers, or other separating objects used in shipping or distribution or food products are efficiently cleaned using a steam cleaning and conveying system. The system can comprise a steam generator, one or more steam cleaning units where optionally an individual object or layer pad is cleaned one at a time, one or more drying units, and specialized conveying and holding units for moving objects through a cleaning apparatus, and then subsequently drying and handling or storing the objects for future use.

21 Claims, 18 Drawing Sheets

(51) Int. Cl.
  *B07C 5/342* (2006.01)
  *G01N 21/94* (2006.01)
  *B08B 9/46* (2006.01)
  *B08B 9/08* (2006.01)

(52) U.S. Cl.
  CPC .............. *B08B 9/46* (2013.01); *G01N 21/94* (2013.01); *A61L 2202/15* (2013.01); *A61L 2202/23* (2013.01); *B08B 2230/01* (2013.01)

(58) Field of Classification Search
  USPC ...... 134/184, 72, 1, 10, 26, 30, 32, 61, 108, 134/15, 37, 64 R, 122 R; 422/26, 298, 422/297, 299, 300, 105, 302; 198/495, 198/601, 339.1, 494, 570
  See application file for complete search history.

(56) References Cited

U.S. PATENT DOCUMENTS

| | | | | |
|---|---|---|---|---|
| 2,714,892 A * | 8/1955 | Mendenhall | ............ | B08B 3/022 134/72 |
| 3,656,493 A * | 4/1972 | Black | ............ | B41F 35/001 134/113 |
| 3,675,665 A * | 7/1972 | Sadwith | ............ | B08B 9/0861 134/46 |
| 3,694,847 A * | 10/1972 | Hetman | ............ | B08B 11/00 15/302 |
| 3,739,790 A * | 6/1973 | Gudz | ............ | A47L 15/242 134/60 |
| 3,990,571 A * | 11/1976 | Kitterman | ............ | B08B 13/00 198/395 |
| 4,104,080 A * | 8/1978 | Sadwith | ............ | B08B 9/0821 134/152 |
| 4,170,241 A * | 10/1979 | Clapp | ............ | B08B 9/0861 134/104.4 |
| 4,281,675 A * | 8/1981 | Pure | ............ | A47L 15/0092 134/125 |
| 4,338,282 A * | 7/1982 | Motooka | ............ | D06F 95/00 134/15 |
| 4,344,448 A * | 8/1982 | Potts | ............ | B08B 3/02 134/108 |
| 4,641,672 A * | 2/1987 | Lewbart | ............ | A47L 15/245 134/127 |
| 5,372,153 A * | 12/1994 | Dobson | ............ | B08B 3/022 134/107 |
| 5,372,651 A * | 12/1994 | Kodama | ............ | B08B 1/04 134/1 |
| 5,446,942 A * | 9/1995 | Whitehorn | ............ | B08B 3/022 134/30 |
| 5,464,595 A * | 11/1995 | Finnah | ............ | A61L 2/07 422/25 |
| 5,593,507 A * | 1/1997 | Inada | ............ | B08B 3/041 134/1 |
| 6,021,790 A * | 2/2000 | Yoshitani | ............ | B08B 1/02 134/62 |
| 6,129,099 A * | 10/2000 | Foster | ............ | B08B 1/02 134/111 |
| 6,143,092 A * | 11/2000 | Straub | ............ | D21F 1/32 134/1 |
| 6,177,677 B1 * | 1/2001 | Alboresi | ............ | A61L 2/08 250/453.11 |
| 6,244,279 B1 * | 6/2001 | Bowden | ............ | B08B 3/041 134/111 |
| 6,264,889 B1 * | 7/2001 | Tottenham | ............ | A23B 7/0053 134/18 |
| 6,451,126 B1 * | 9/2002 | Mattix | ............ | B08B 3/02 134/199 |
| 7,287,535 B2 * | 10/2007 | Kataoka | ............ | B08B 3/02 134/111 |
| 8,273,186 B2 * | 9/2012 | Rubenzer | ............ | D06G 1/00 134/122 R |
| 8,277,566 B2 * | 10/2012 | Rubenzer | ............ | D06G 1/00 134/15 |
| 8,795,439 B2 * | 8/2014 | Vernon | ............ | B08B 1/005 134/122 R |
| 2001/0026826 A1 * | 10/2001 | Tottenham | ............ | A23B 7/0053 426/521 |
| 2002/0153021 A1 * | 10/2002 | Audet | ............ | A47L 15/0015 134/1 |
| 2003/0203116 A1 * | 10/2003 | Brown | ............ | D06G 1/00 427/385.5 |
| 2005/0106355 A1 * | 5/2005 | Kohlman | ............ | D06B 11/0059 428/85 |
| 2005/0123435 A1 * | 6/2005 | Cutler | ............ | A23L 3/001 422/1 |
| 2007/0051585 A1 * | 3/2007 | Scott | ............ | B65G 47/54 198/370.07 |
| 2007/0170040 A1 * | 7/2007 | Handy | ............ | B08B 1/008 198/495 |
| 2007/0227562 A1 * | 10/2007 | Lee | ............ | B08B 1/02 134/34 |
| 2008/0110474 A1 * | 5/2008 | Weinstein | ............ | D21F 1/32 134/15 |
| 2011/0108070 A1 * | 5/2011 | Kunnas | ............ | B08B 1/02 134/32 |
| 2011/0262319 A1 * | 10/2011 | Svensson | ............ | A61L 2/07 422/298 |
| 2013/0269734 A1 * | 10/2013 | Hunter | ............ | B08B 11/00 134/32 |
| 2014/0000648 A1 * | 1/2014 | Ingle | ............ | A61L 2/07 134/1 |

* cited by examiner

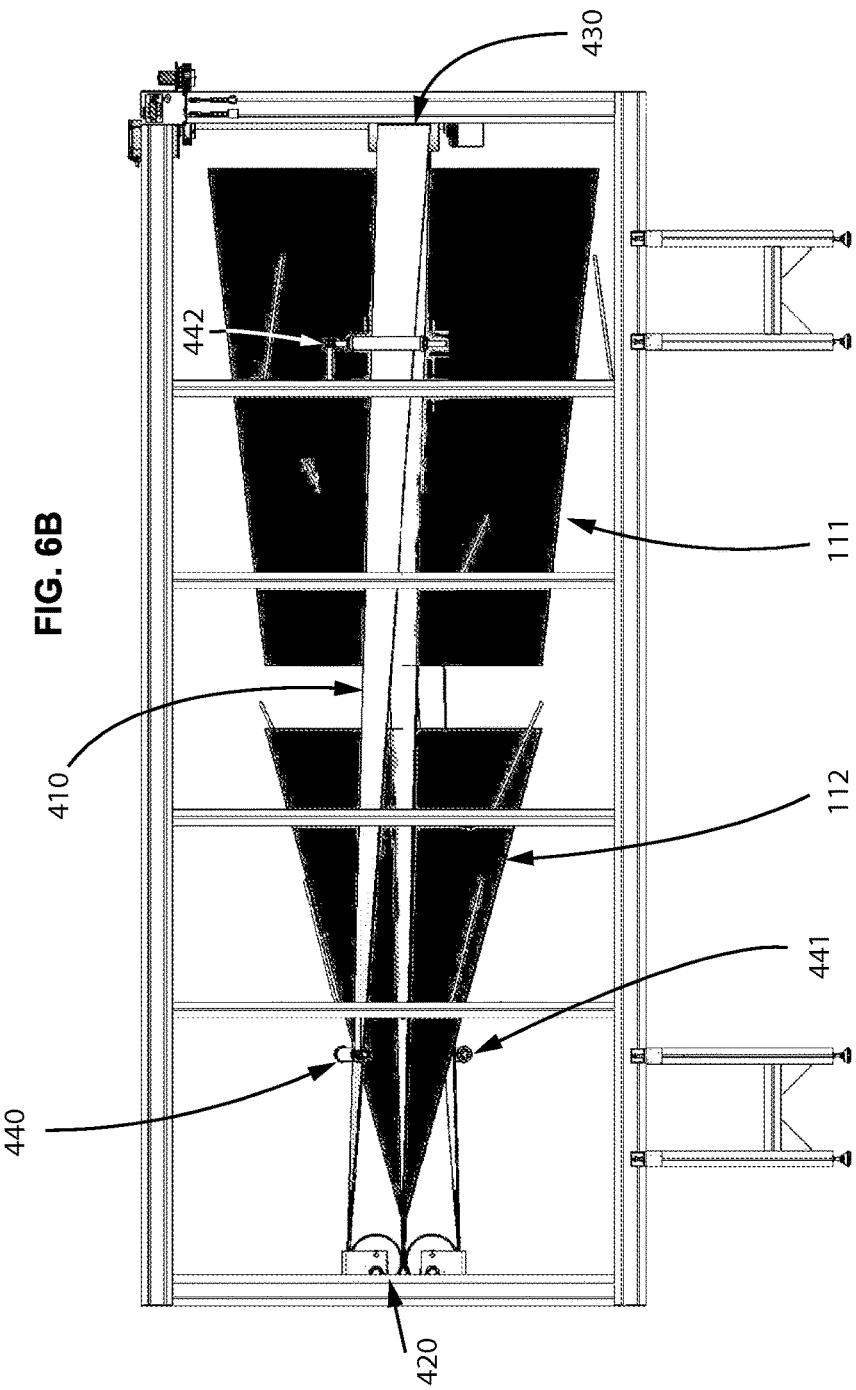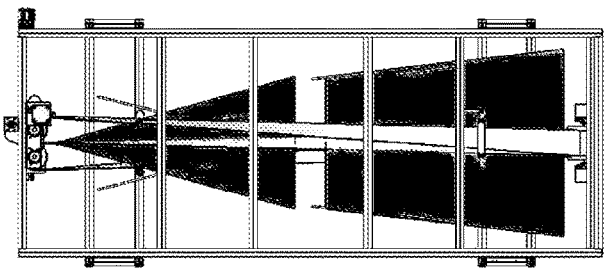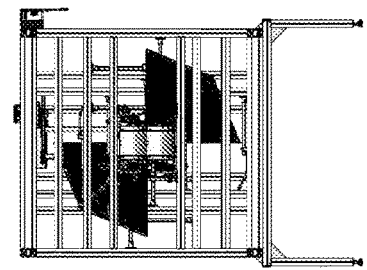

FIG. 12A
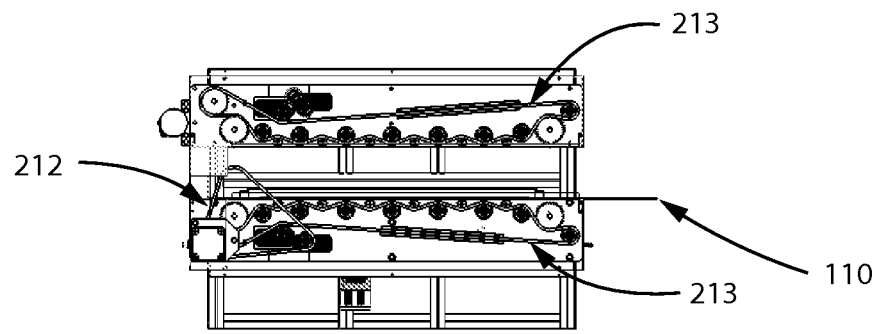
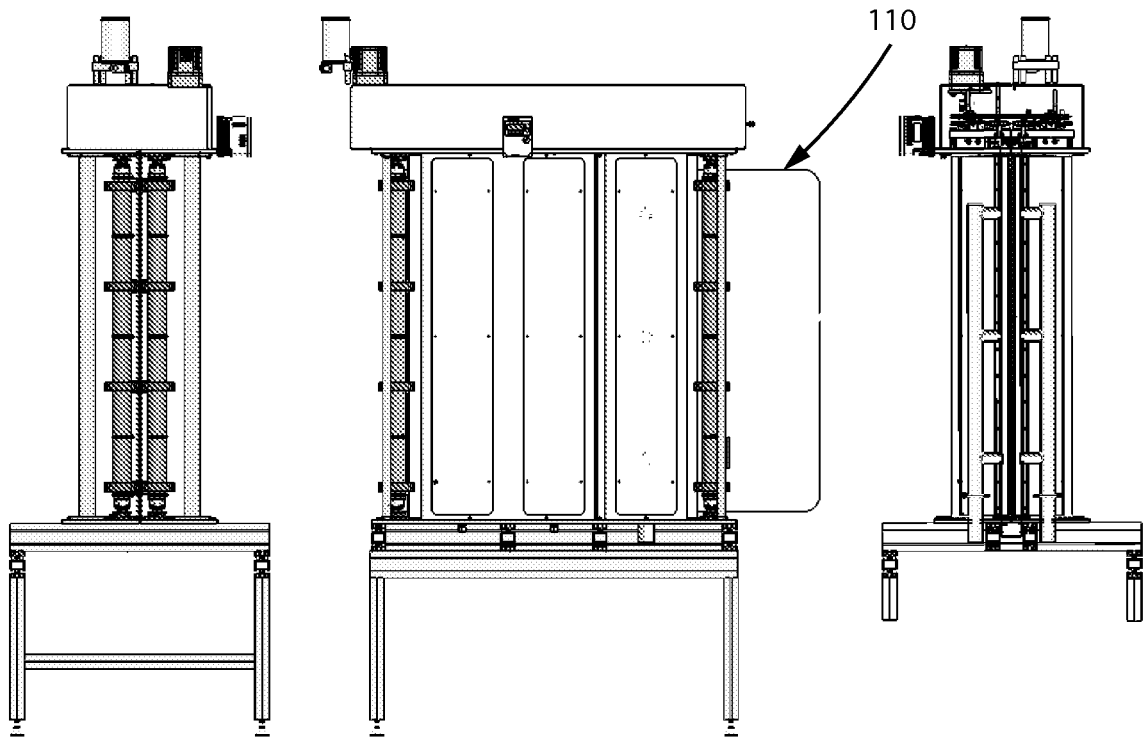
FIG. 12B   FIG. 12C   FIG. 12D

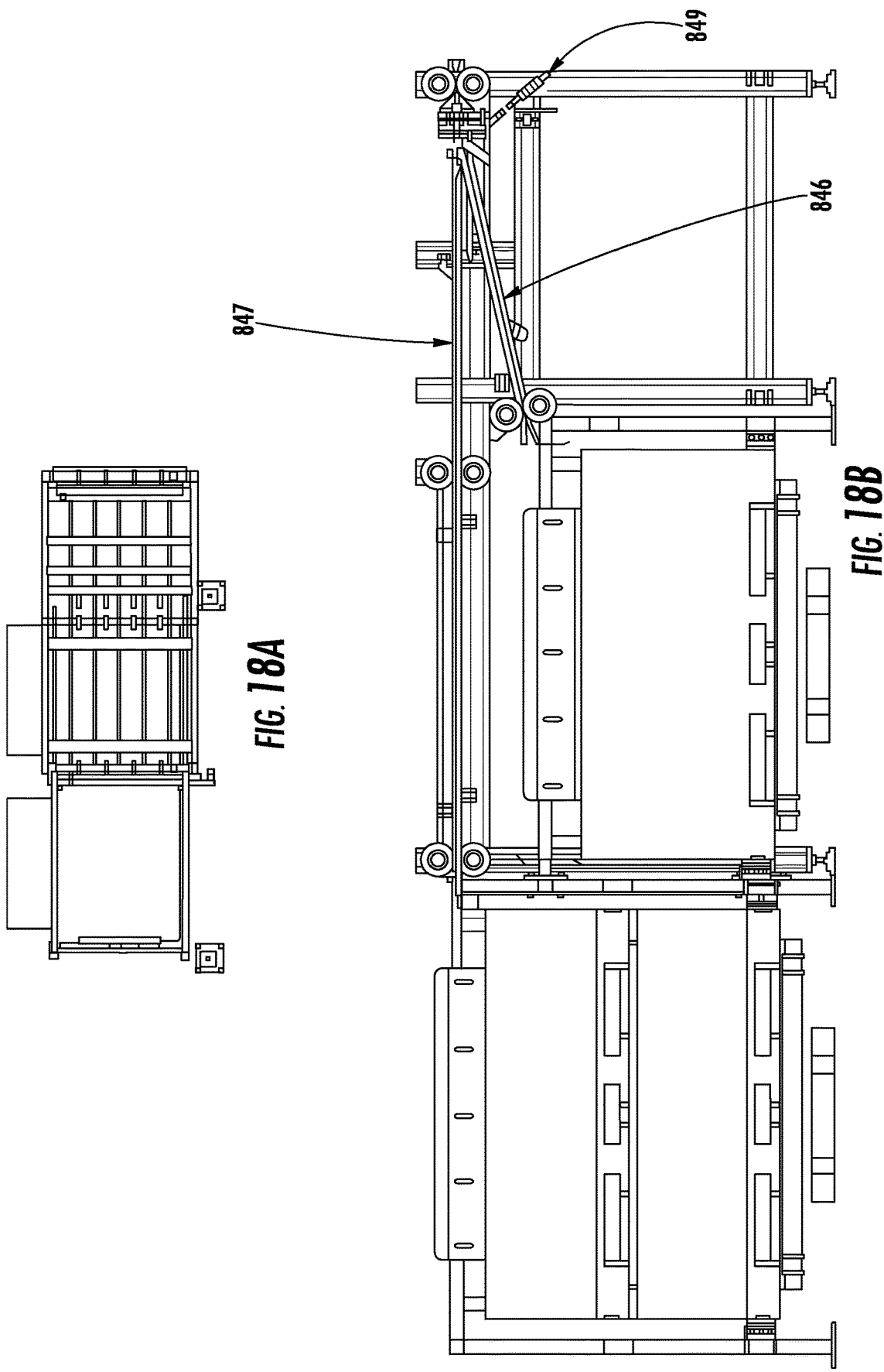

CONVEYING AND CLEANING SYSTEM AND METHODS FOR CLEANING AND STACKING TRAYS AND/OR LAYER PADS

FIELD OF THE INVENTION

Field of the Invention and Introduction

The present invention relates to a system for cleaning layer pads or other barriers or containers that can be used in stacking products that are typically shipped or stored in a standard container setting. Commonly used plastic and corrugated layer pads are an example of widely used separating pads for this purpose, especially with palletized products and packages. In particular, the invention relates to a system employing high temperature steam to clean layer pads in an automated and efficient manner, or alternatively to steam clean containers typically used in the food manufacturing or food services industries. The system can optionally stack the cleaned pads or containers for storage. Even more particularly, the present invention relates to devices and methods for conveying layer pads and containers through a conveying device for quality control checks as well as cleaning them so that they can be re-used without fear of contamination.

Layer pads are used in a number of industries for stacking products efficiently and safely on pallets. What is needed, therefore, is a system and method for cleaning these layer pads so that they can be re-used. However, the reused layer pads, especially if used for the food service industry, should be clean and free of contamination.

BRIEF SUMMARY OF THE INVENTION

The present invention meets these and other objectives by providing devices and methods for cleaning and inspecting layer pads or alternatively containers at a high rate and with high efficiency. One advantage of the present invention is that it facilitates the handling of layer pads and allows for the reuse of layer pads with a higher degree of cleanliness, a lower defect or waste rate, and greater confidence in industries where contamination or cleanliness are important.

Another advantage of the present invention is that it minimizes the risk of damaging food or other products designed to be stored or shipped in a palletized manner.

A further advantage of the instant invention is that it facilitates removal of noncompliant containers or layer pads while simultaneously cleaning them for further use.

In one aspect, the invention encompasses a system for conveying, inspecting, and steam cleaning plastic layer pads, where the system contains several handling or treating stations in sequence. Generally, the sequence is important but alternative sequencing of the stations is possible beyond those exemplified here. The system comprises one or more conveying and vertical handling devices for moving a single layer pad from a supply stack toward a steam cleaning station, where the one or more conveying and handling devices are capable of orienting the single layer pad into a vertical or horizontal/parallel position. For example, the flat surfaces of the layer pad can preferably be perpendicular to the ground. The steam cleaning station is connected to a steam generator for providing steam of at least 160 degrees F. to produce temperatures on the surfaces of the layer pad of 160 degrees F. for a desired period of time. The steam cleaning station can containing one or more than one steam treating units oriented toward each vertical side of the layer pad, where steam is directed toward the layer pad from multiple sources of the steam treating unit, and wherein the one or more steam treating units substantially seal a section of the layer pad surface within the steam region defined by the unit. Thus, the steam can contact and treat a section of the layer pad surface for a desired amount of time to bring that section of the layer pad surface into a desired temperature or sterilized condition. An optional drying station is positioned after the steam cleaning station and the drying station removes excess moisture on the pads after the cleaning process through, for example, the operation of one or more air knives and/or with multiple consecutive wiper sections. The combined effect of wiping and blowing air on the pads sequentially dry the layer pads until all moisture is removed before stacking. An inspection station comprising at least one visual detection device for inspecting each of the surfaces of the layer pad also is positioned after the steam cleaning station. This can include a system for evaluating the surfaces of the layer pad and tracking the movement of the layer pad associated with both surfaces. A sorting station for sorting individual layer pads is positioned after the steam cleaning station and the inspection station, and the sorting station capable of responding to the tracking the movement of the layer pad from the inspection station in order to direct each layer pad into one or multiple sort stacks. Thus, for example, adequately cleaned layer pads can be sorted to a "pass" stack where inadequately cleaned layer pads can be sorted to a "reject" stack.

In another alternative aspect, the steam cleaning apparatus is used to deliver a single container for cleaning at a time, where the handling of the container does not prevent the cleaning of all the internal services. For example, a flexible device for securing or maintaining the container in a position for cleaning is used so that steam and/or cleaning conditions can contact all parts of the container. In addition, multiple contact points for holding the container can be used to ensure that all surfaces of the container are effectively exposed to cleaning conditions or exposed to the desired steam and temperature conditions for disinfection, as noted with the temperatures above. The foregoing and other aspects, features, details, utilities, and advantages of the invention will be apparent top one of skill in the art from the following description and claims, and from a review of the accompanying drawings.

BRIEF DESCRIPTION OF THE DRAWINGS

FIGS. 5, 6A, 6B, and 6C depict an exemplary horizontal to vertical flipping device guided by belts in this case.

FIGS. 10A, 10B, 11A, 11B, 12A, 12B, 12C, 12D depicts various views of the washing section or superheated steam cleaning section.

A drying station is optionally inserted into the conveyor line after the cleaning section.

Figure 13:
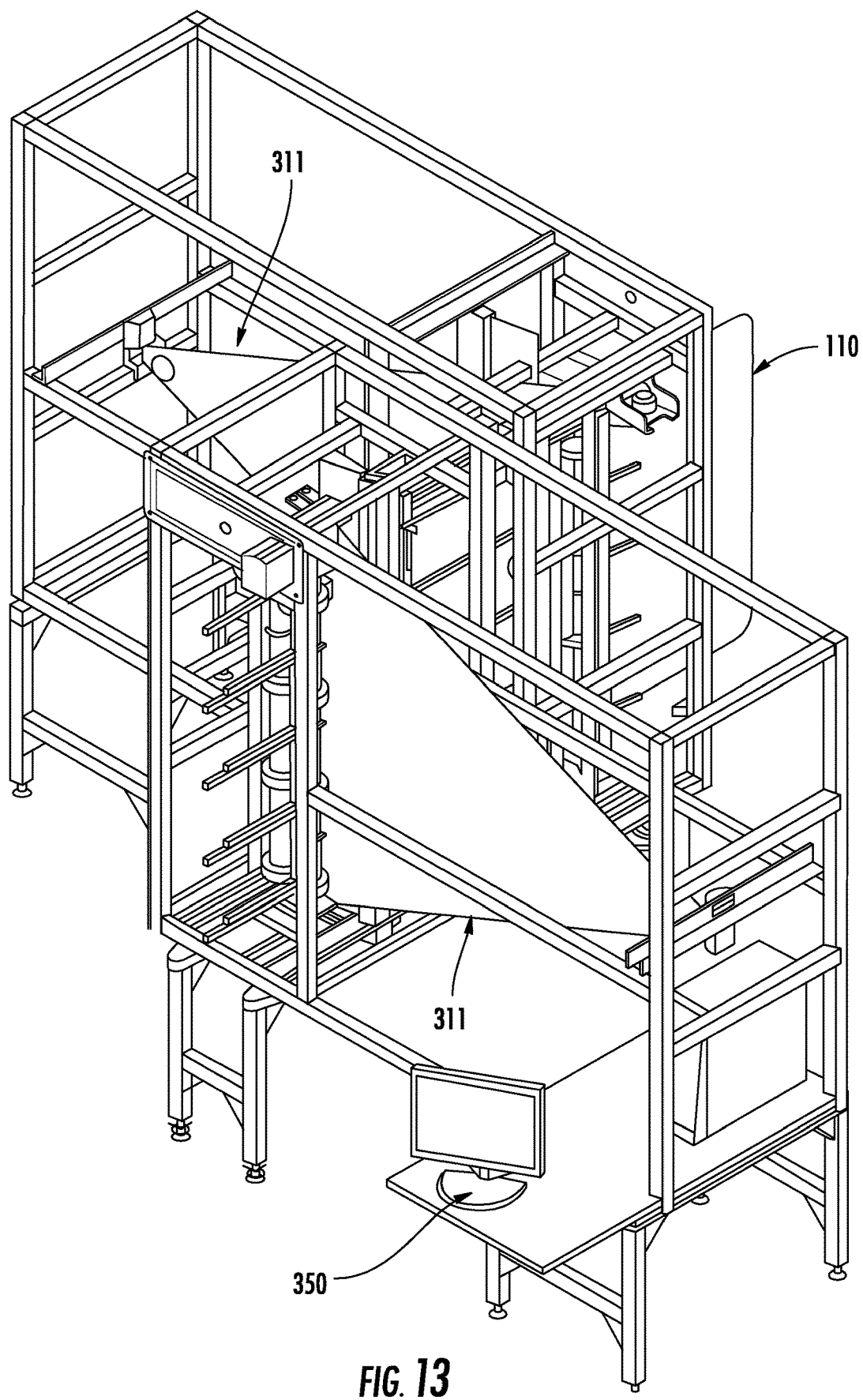
Figure 14:
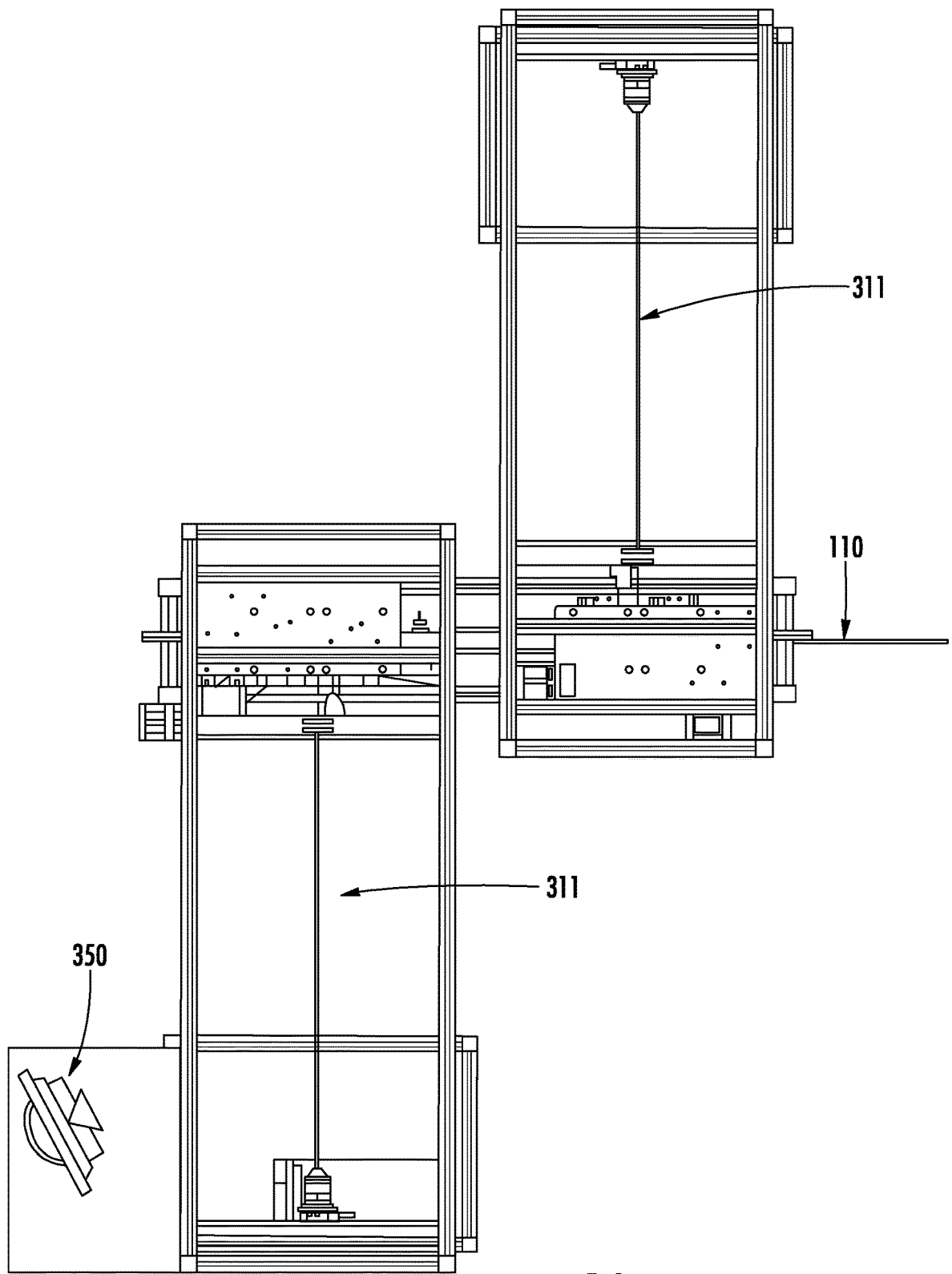

FIGS. 13 and 14 depict an inspection station in different views.

Figure 15:
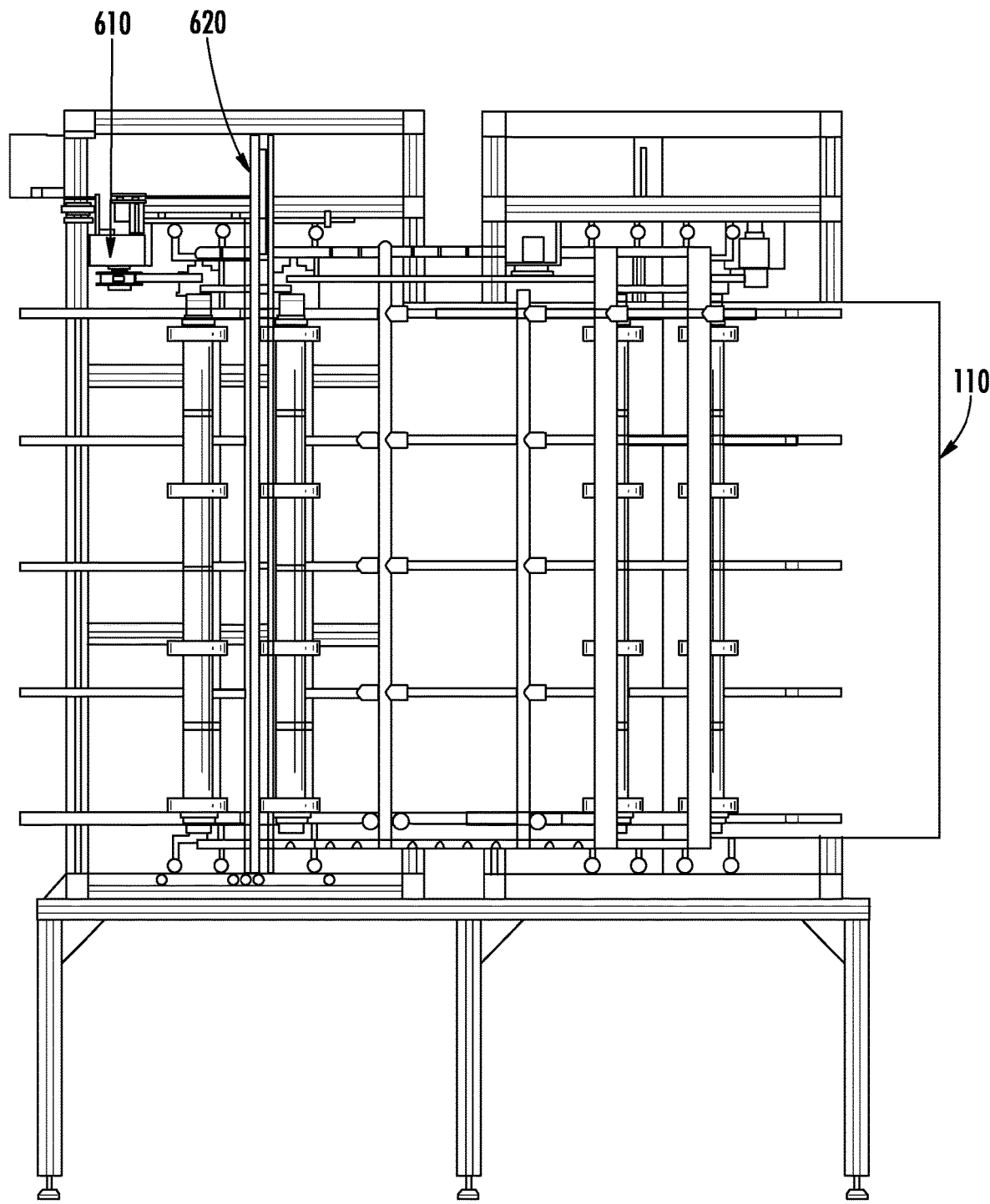

FIG. 15 depicts a vertical conveying section.

FIGS. 16, 17, 18A, and 18B depict the final sorting/stacking station, where layer pads or flats are sorted into two or more groups. In one example, the layer pads are sorted into "pass" (or "acceptable") and "reject" groups based upon input from inspection station of FIGS. 13 and 14.

DETAILED DESCRIPTION OF THE INVENTION

The present invention provides devices and methods for handling layer pads or flats typically used between layers of stacked goods or packages. In particular, the invention includes cleaning and inspection stations in a system of cleaning and conveying flats or layer pads. As many crated items in the food and food services industry employ flats or layer pad elements to stack one layer of packaged good on top of another, the use of cleaned layering pads becomes more and more important. Any contamination of articles used in shipping and storing food service products can result in delays and expenses.

In one aspect, the system and methods of the invention employ steam to clean layer pads, which advantageously provides both a sanitizing effect as well as a cleaning effect simultaneously and on the same conveyor system. In preferred embodiments, the invention can be developed for use on plastic sheets or layer pads, which tend to repel moisture. In additional embodiments of the invention, the conveyor system can include static electricity brushes to remove unwanted static from plastic layer pads. Coated flats or layer pads can also be similarly cleaned through the system and methods of the invention.

In another aspect, the use of vertical directional conveyance in the invention promotes the removal of dirt, debris, and residual moisture from the pads of flats as they move through the system. In addition, the invention can advantageously use multiple rollers in different directions to ensure that a single layer pad or flat moves into the system at a time. This system has advantages over suction systems for lifting or moving a single pad or flat, as the friction-based movement from rollers here can detect and prevent all but a single layer pad or flat from moving at various points of contact. In addition, the invention as described can operate up to 1800 layer pads per minute, while other systems that contain different combinations of elements can only operate at approximately 600 layer pads per minute.

This system (100) generally begins with an operator preparing a stack of flats to be cleaned and sorted. Any bands, wraps or other extraneous components from a pallet of flats, such as pallets of plastic layer pads, are manually removed. Also, any layer pads that overhang the stack by more than a desired tolerance limit are manually removed.

More than one stack of flats can be used to enter the cleaning system of the invention. In general, a stack height of less than 18 inches is optimal for dual stack induction, or a stack height of less than 40 inches for single stack induction. Dual stacks can be stored one on top of the other if desired.

Figure 2:
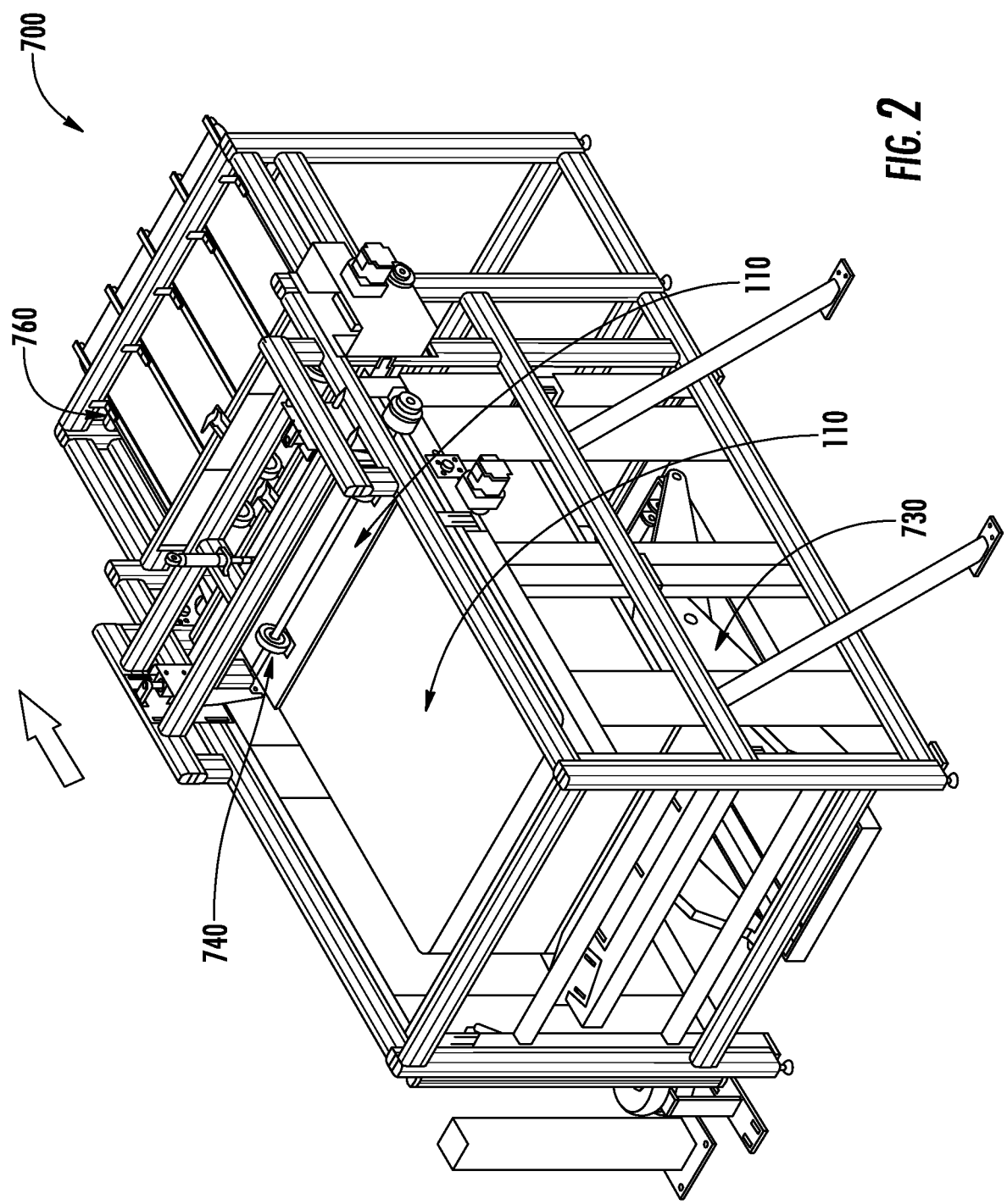
FIG. 2 depicts the receiving, holding and unitizing device. Flat products or layer pads are received, stored, and then separated into a single layer pad or flat unit and sent on to the next handling device.
Figure 3:
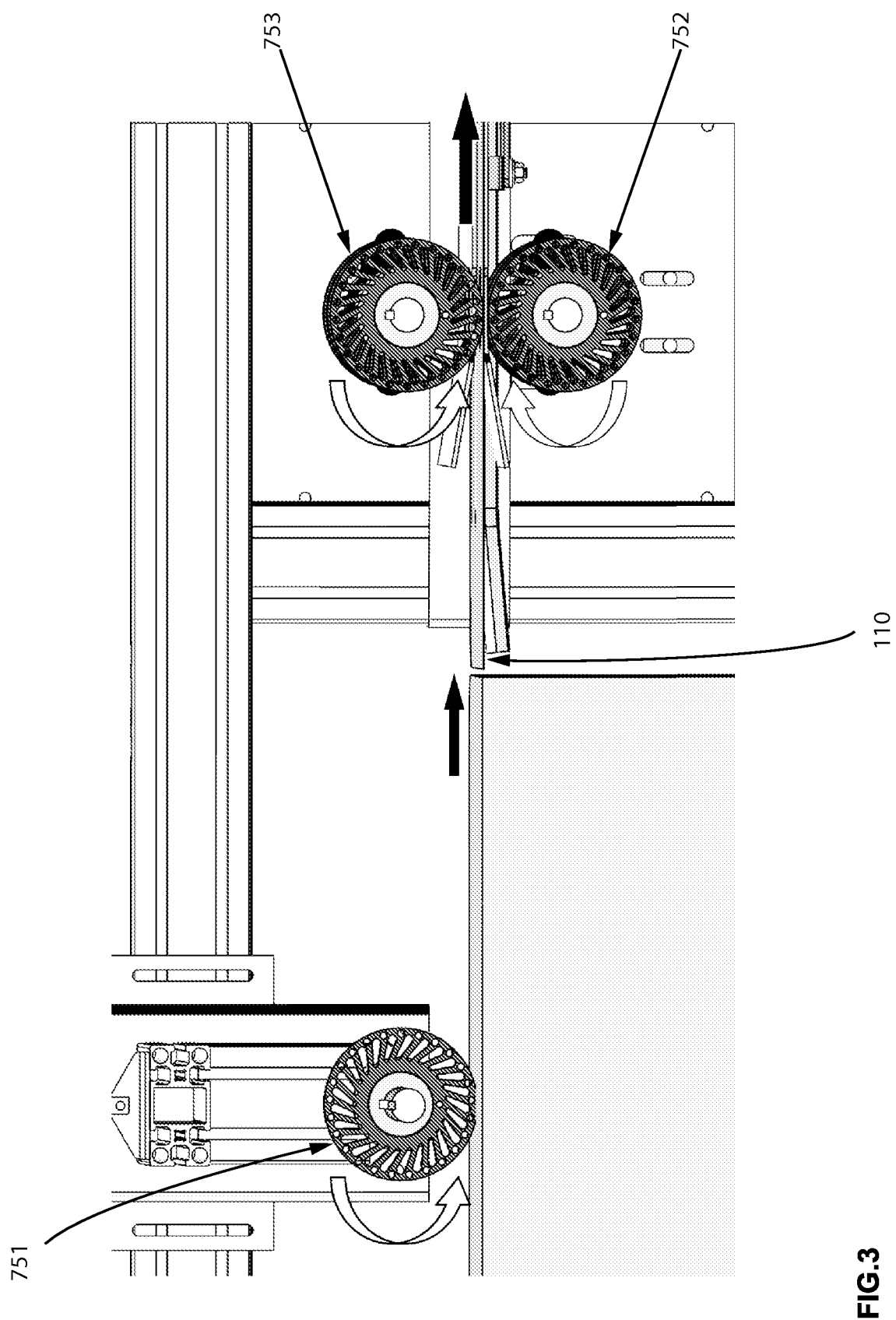
FIGS. 3, 4A, and 4B depict close up views of the device of FIG. 2, where an exemplary apparatus sends one unit of flats or layer pads on to the next device by a system of controlled rollers. The pressure applied from the roller, a clutch system for controlling the speed of the rollers, and the lift of the stack of pads or flats from a scissor lift or any other lift mechanism (ball screw, actuator, etc.) coordinate to send a single unit at a time.
Figure 4:
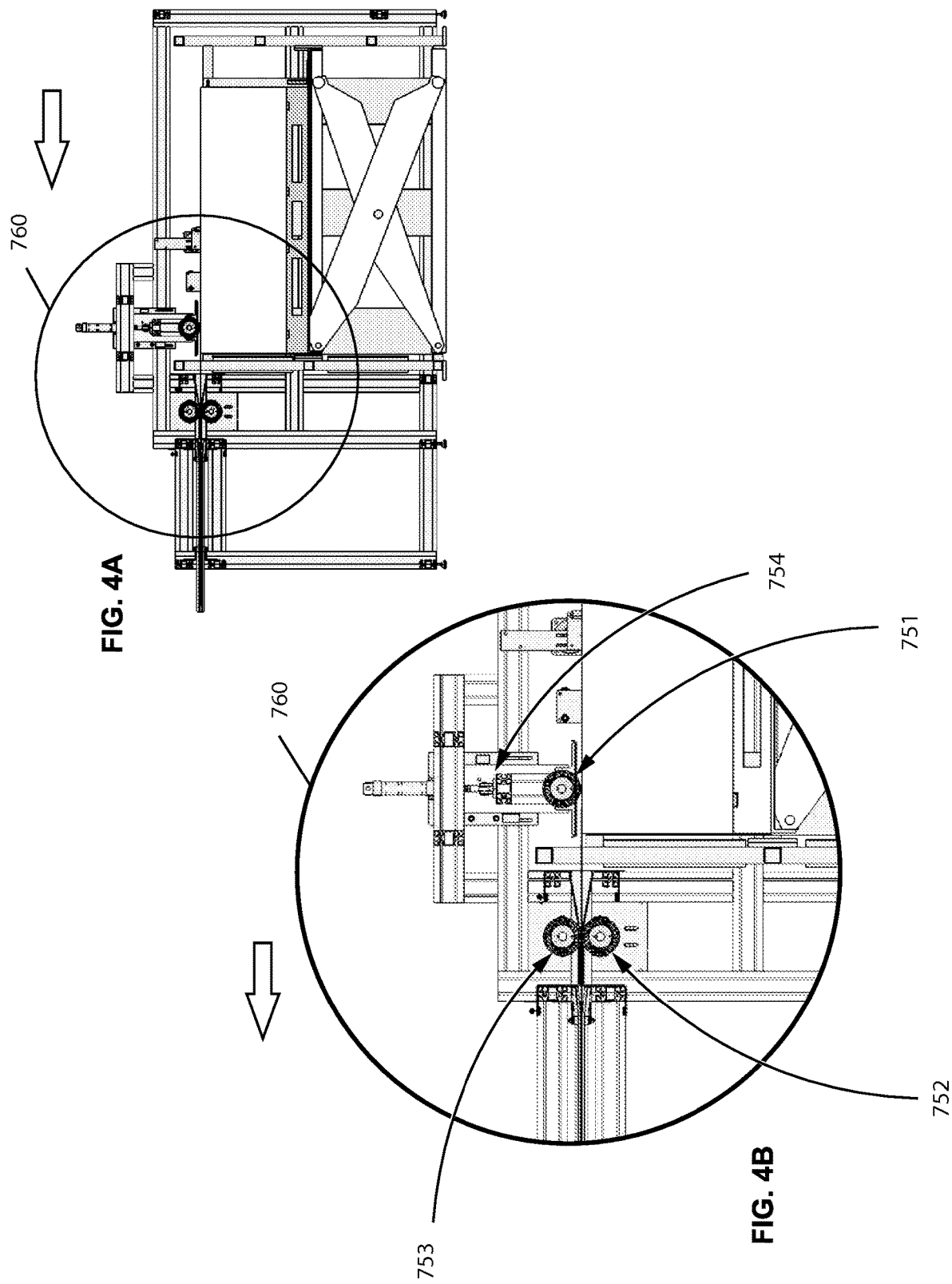

The receiving and loading station (700) singulates and inducts a single layer pad from a stack of layer pads (110) into the system at a time. FIGS. 2-4 show details. A scissor lift in combination with suction cups distributed across the layer pad (110) tensions the pressure of the top layer pad (110) against top roller (740) that moves the layer pad in the direction of the arrow shown in FIG. 2. In FIG. 3 a set of rollers are shown. The first roller (751) is controlled by the system when suction cups lift the layer pad to apply desired pressure to advance a single layer pad (110) of a known thickness. Rollers (753), suction cups, and (752) operate as drive and clutch rollers so that a single payer pad is sent through the area between them at a time. FIG. 4B shows a close up of area (760) of FIG. 4A. Controlling unit (754) includes a piston for controlling the applied downward pressure of the suction cups.

Figure 5:
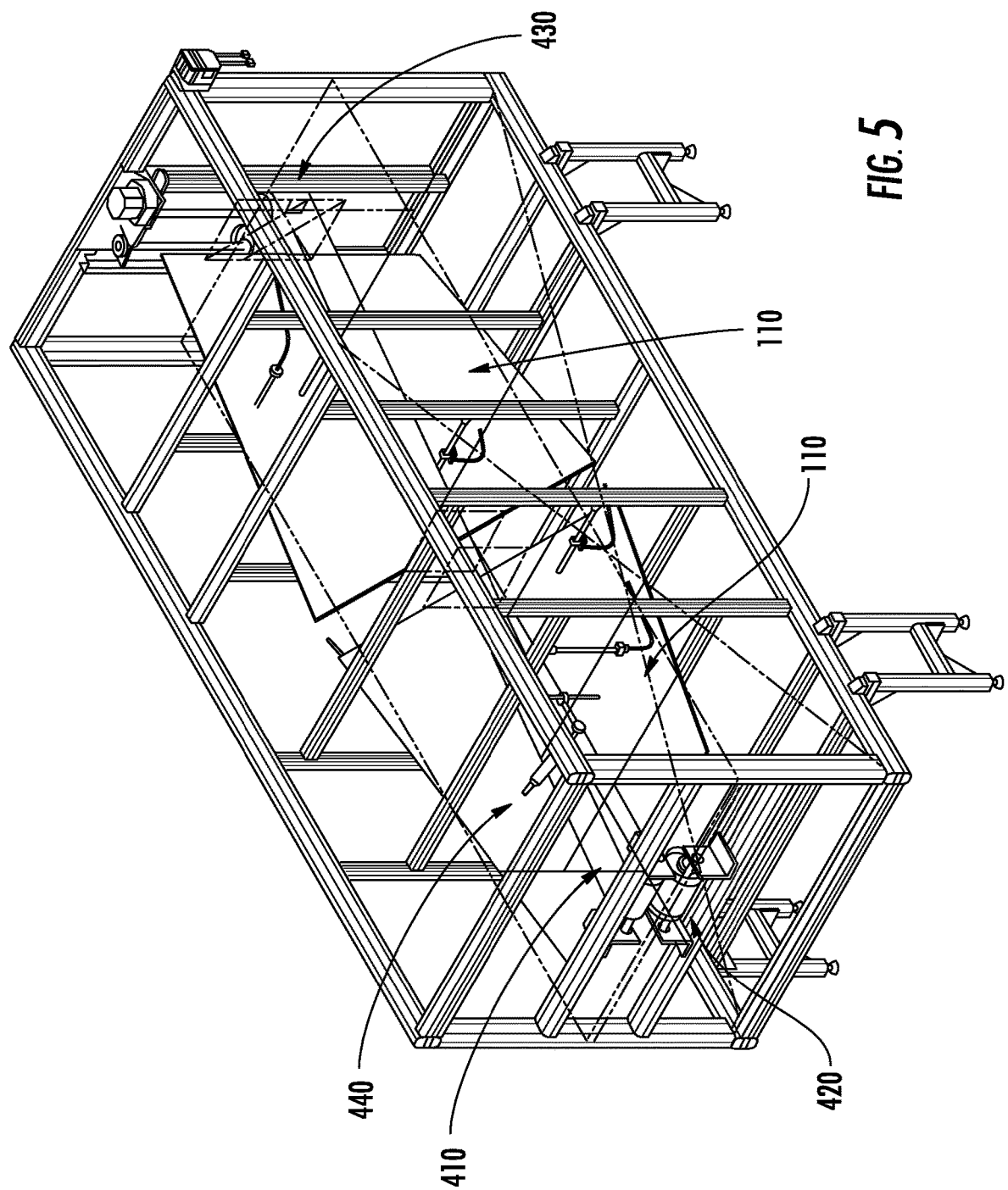
Figure 7:
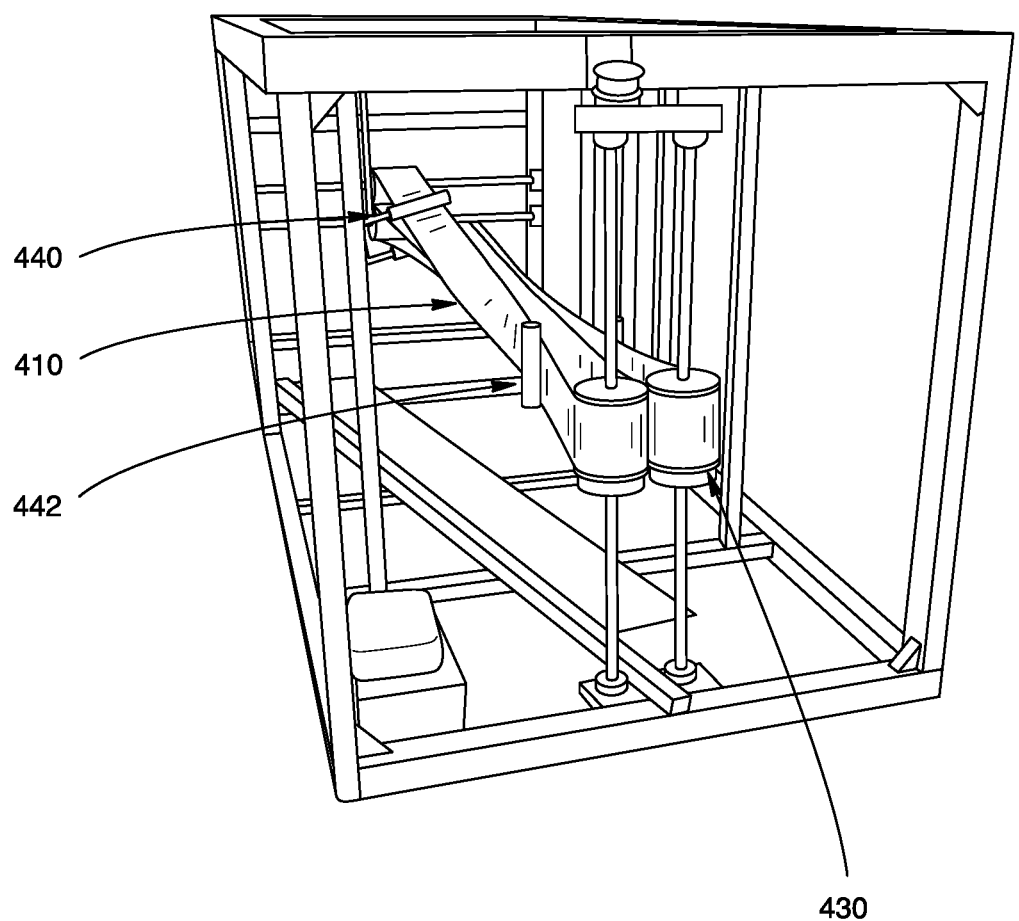
FIGS. 7 and 8 show photographs of the belt systems depicted in the example of FIGS. 5, 6A, 6B, and 6C.
Figure 8:
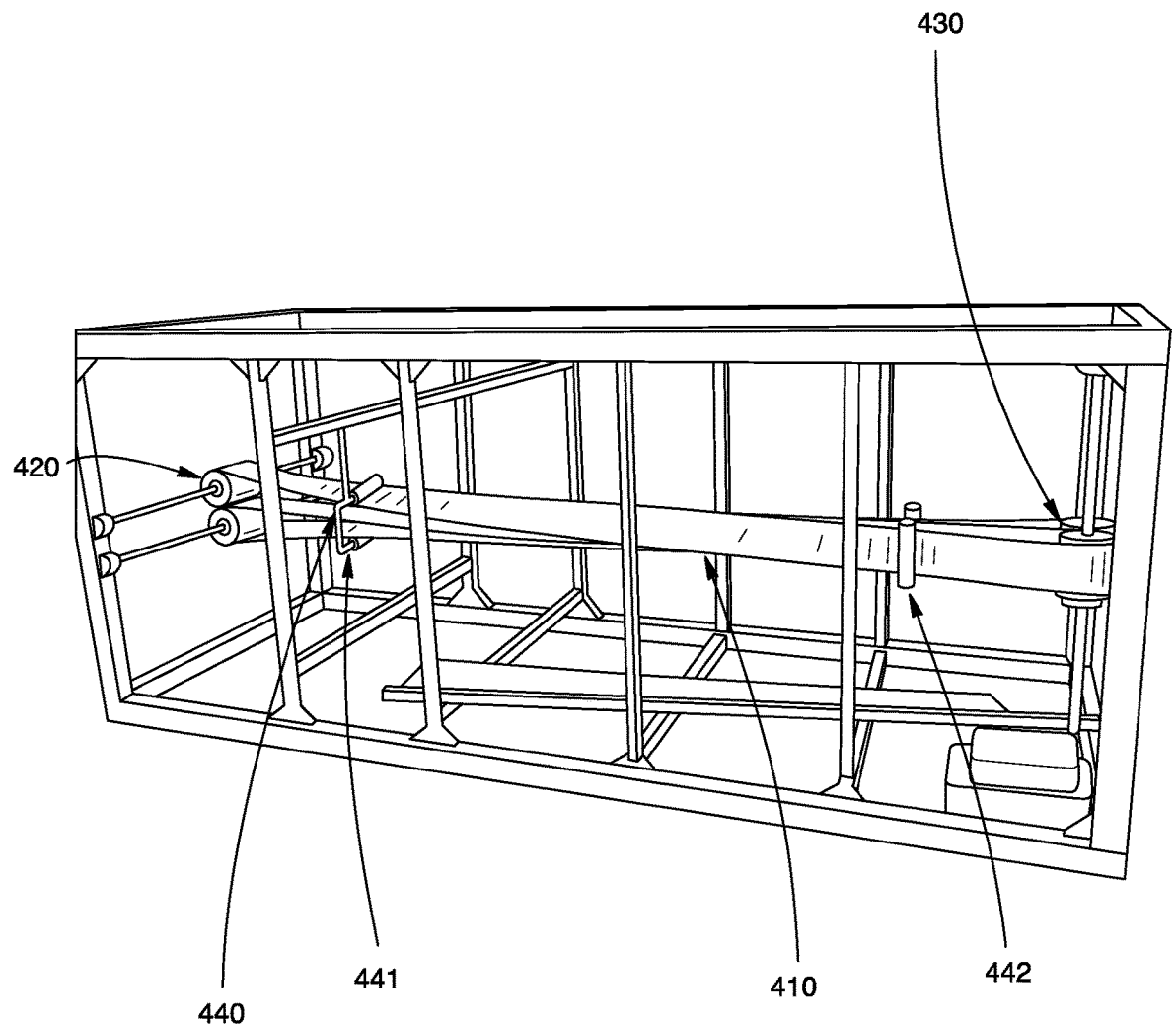
Figure 9:
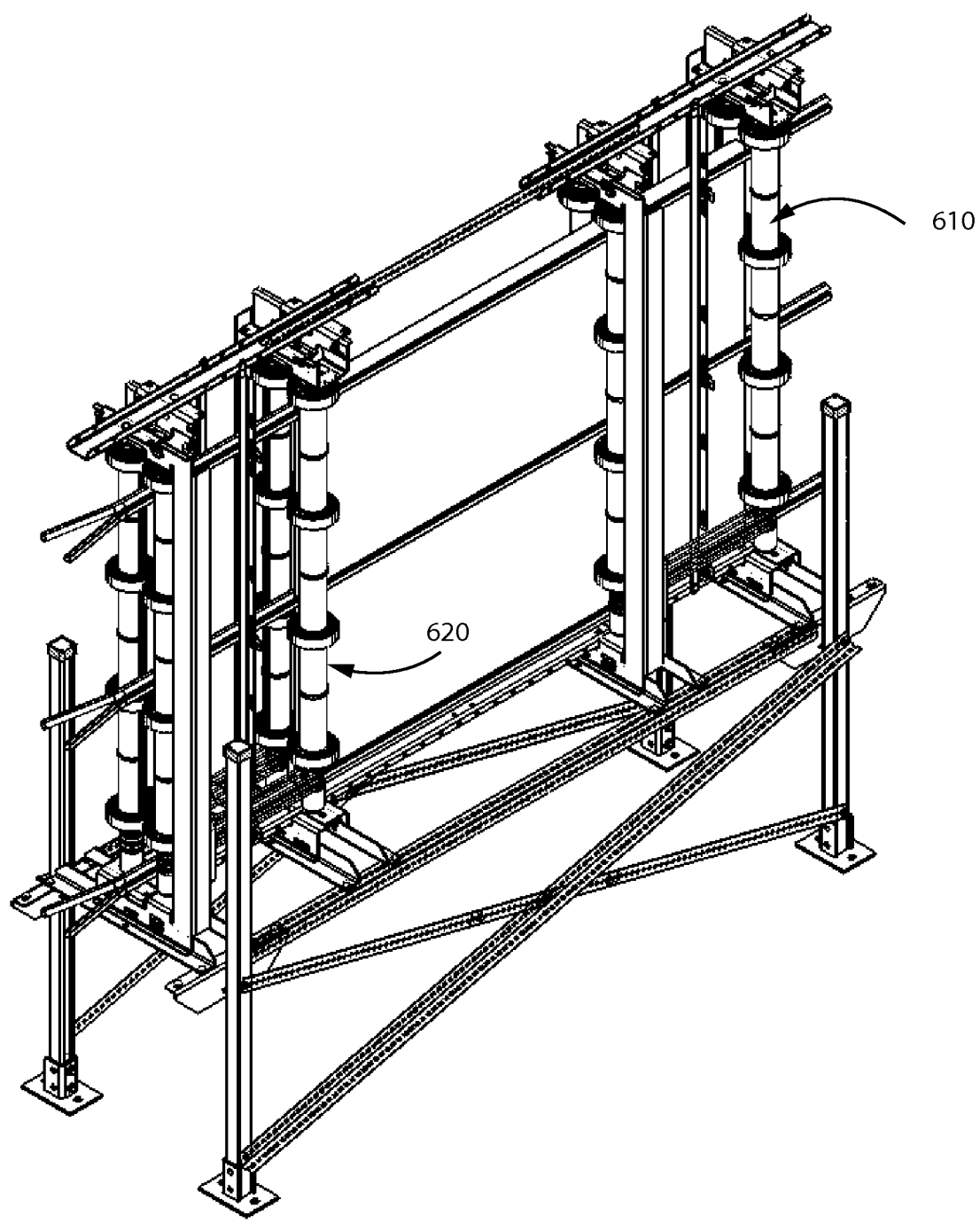
FIG. 9 illustrates a vertical conveying section.

Each single layer pad (110) is flipped from its initial horizontal orientation in the stack, horizontal with respect to the flat surfaces of the layer pad, to the vertical position by flipper station (400). FIGS. 5-8 depict an embodiment of a flipper station. Sets of belt rollers (420) and (430) at each end of the station are oriented 90 degrees different from one another. This creates a 90 degree twist in belt (410) as it moves from one end to the other. Each of the two rollers shown in (420) and (430) contain a belt (410), so that two belts span the two ends of the flipping station as shown in FIG. 5. Belt tensioners (440) are used to maintain tension of the belt through the station and keep the layer pad from slipping out of orientation. Justifiers and guide rails are used as guides to ensure that the bottom edge of the layer pad stays within desired parameters and that the layer pad leaves the station properly positioned. FIG. 6B shows the two sets of belts (410) as they twist from one end to the other. Belt tensioners (440) (441) and (442) are positioned where desired. The black layer pad (110) is shown in the process of being flipped to vertical while layer pad (110) is now in vertical position ready to exit the station at rollers (430). FIGS. 6A and 6C shows alternative views of the two layer pads while progressing through the station. FIGS. 7 and 8 show photographs of a flipper station without the layer pads in them. All of the belts, belt rollers, tensioners mentioned above are shown. FIG. 9 shows a vertical conveying station, or Vertical Flats Conveyor VFC, where the layer pads brought into vertical orientation are moved between rollers (610) and (620). Between modules, justifiers and guide rails are used to transition product without jams.

Figure 1:
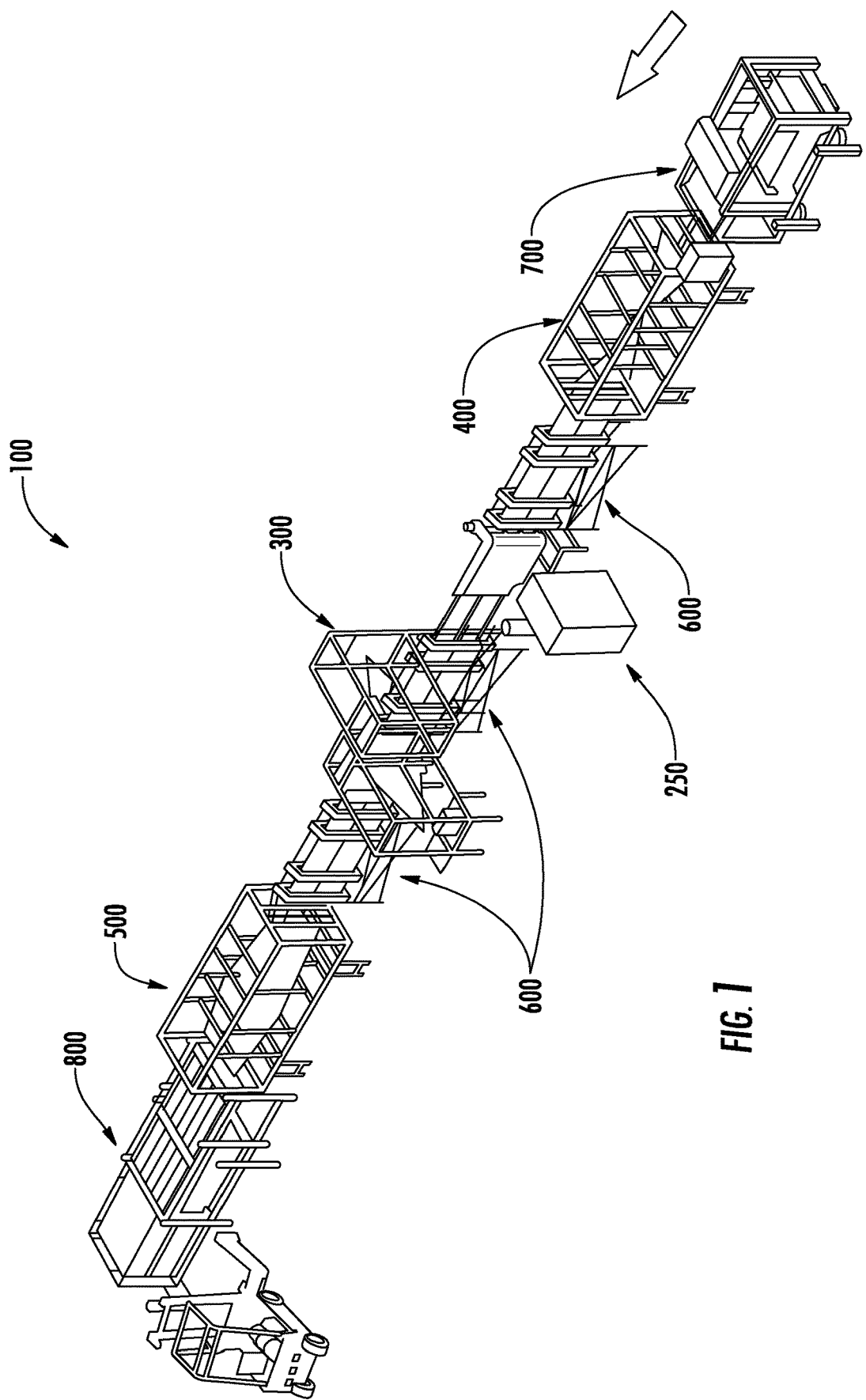
FIG. 1 depicts an exemplary configuration of sections or stations in a layer pad or flats handling and cleaning device, where layer pads or flats are directed from the end with the arrow to the other end. The sections include, beginning from the side with an arrow: receiving/unitizing station; horizontal to vertical flipper station; vertical conveying station or VFC; washing or super-steam cleaning station with associated boiler and superheater; drying station; inspection station; vertical conveying station; vertical to horizontal flopping station; sorter/stacker station.
Figure 10B:
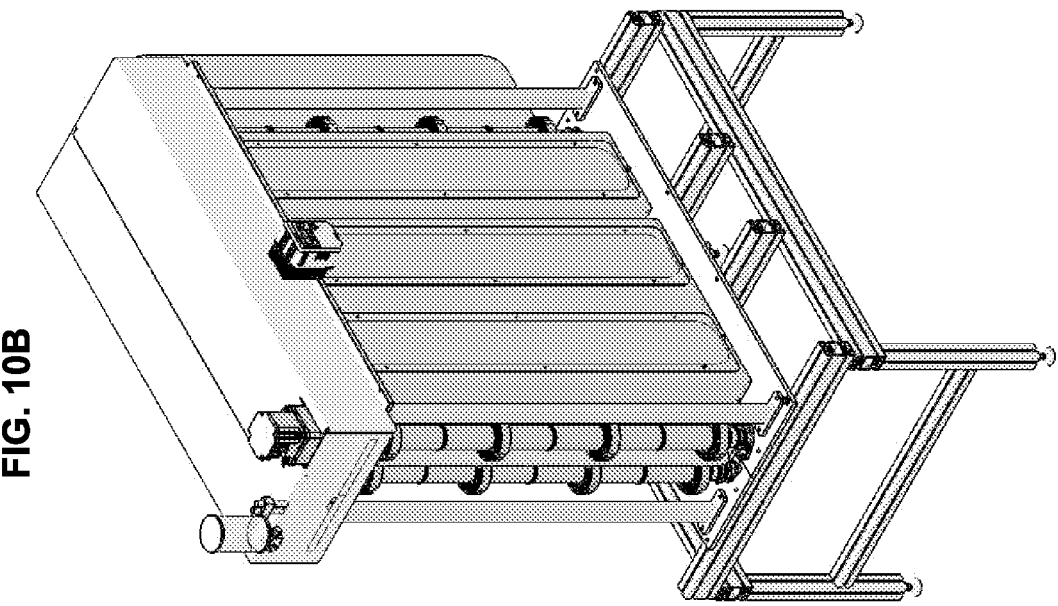
Figure 10A:
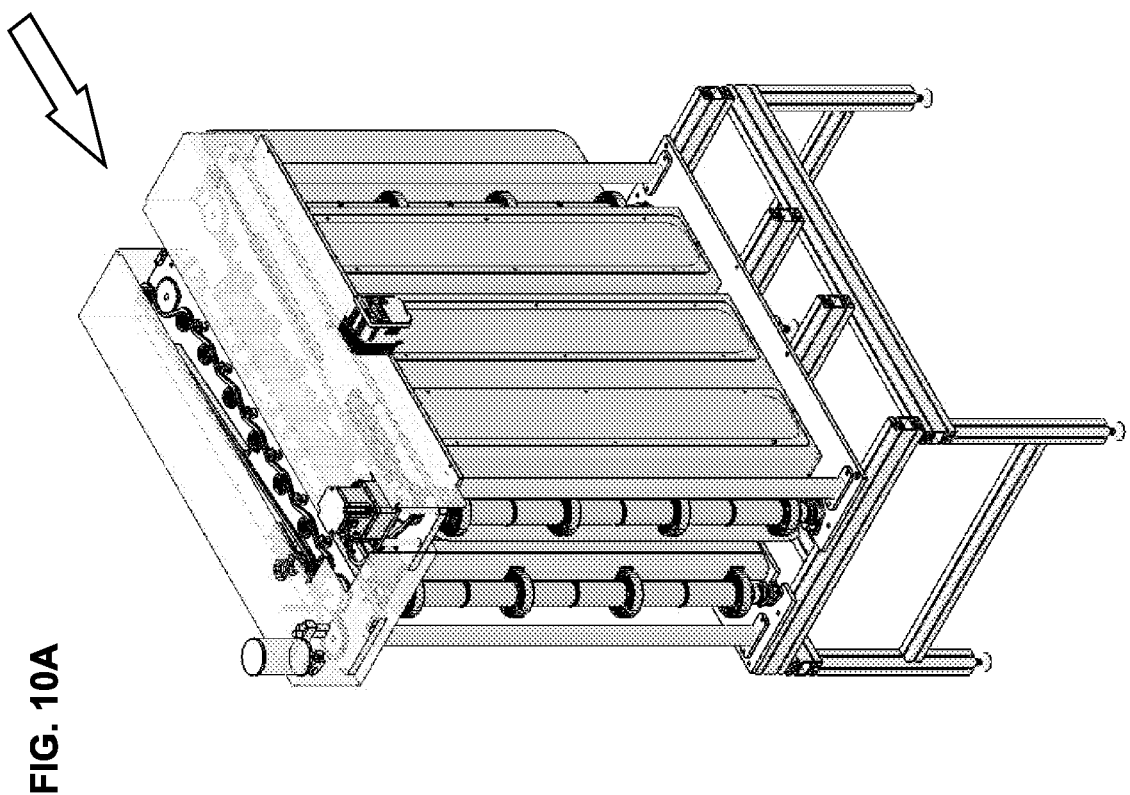
Figure 11B:
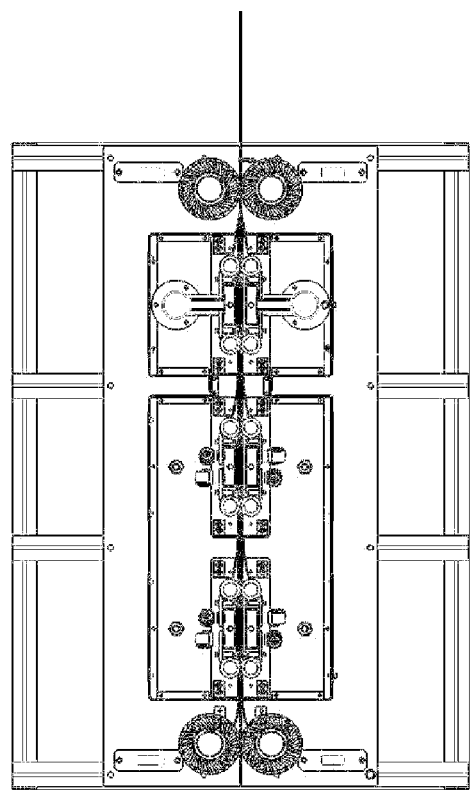
Figure 11A:
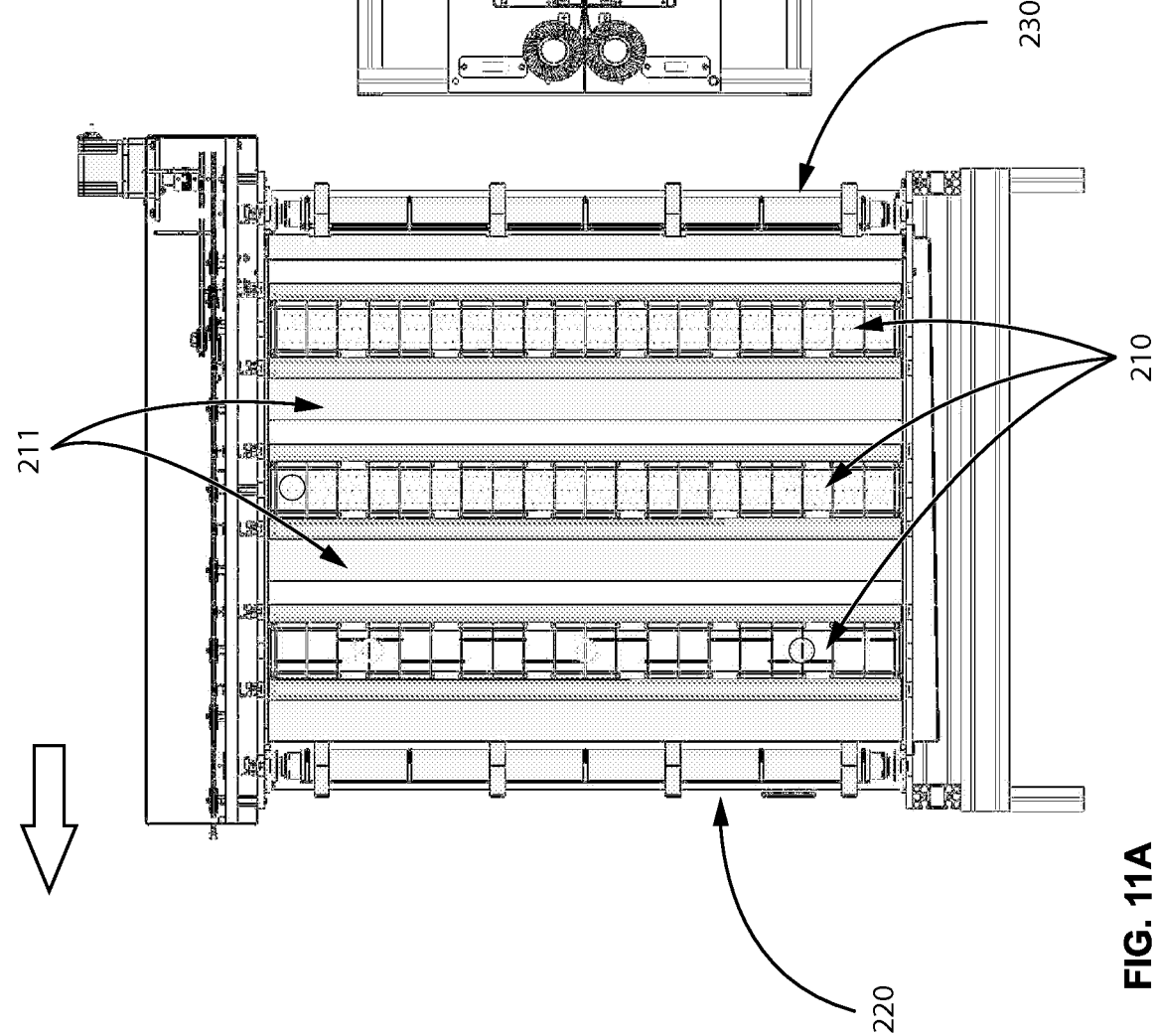

FIGS. 10-12 show various parts and views of the steam cleaning station. As shown in FIG. 1, steam generator (250) provides instantaneous steam from a high power boiler and superheater. Because of the speed at which flats or layer pads move through the system, steam generation must by consistent and continuous once the system is in operation. In operation, the steam cleaning station is designed to steam clean simultaneously all the surfaces of both sides of the layer pad. FIG. 11A shows in detail one embodiment of a steam cleaning station. Sets of steam treating units (210), where the rollers are made of silicone or a similar polymer or silicone combination rollers, use tensioned rollers to create one or more sealed, steam-treating regions between them and the layer pad. Sealing surfaces on the rear surface of the rollers provide a sealed compartment for steam and vacuum sections. The length of the units (210) covers the length of the flat surface of the layer pad or flat being sterilized or cleaned. Between each set of rollers in the units (210) are steam outlets spaced from top to bottom and side to side. To ensure that the layer pad remains flat during its progress through the station, the areas between the units (210) contain flat plates (211). Plastic layer pads have a tendency to curl when heated and the combination of rollers on units (210) and wire guides and flat plates (211) and their placement keep the layer pad flat. Additional rollers (220) and (230) provide tension at the ends of the station. Multiple steam treating devices as shown in FIG. 11A can be used in sequence to ensure proper cleaning. FIG. 12 depicts additional aspects. In FIG. 12A, chains (213) apply pressure on each side of the unit while chain (212) applies pressure of one side of the unit against the other. In combination, the rollers as discussed above for units (210) can create one or more sealed regions for steam treatment or sterilization. Vacuum manifolds port excess moisture and debris out of the wash unit through suction slots and holes, thereby sealing the cavity through rollers and sealing covers. The steam exhausts out of vacuum manifolds as well as the steam section covers through rigid or flexible tubing. Excess moisture will condense within the steam system and is ported to a drain through weep holes and drains.

An exemplary drying station can be included after the washing section. This station uses various drying devices including wipers and air knives to dry the layer pads as they traverse through the system. In preferred embodiments, the layer pads move close to air knives for drying and are maintained through mesh guiding to keep from straying due to the intense air pressure. The locations, air pressure, and angles of air knives all contribute to effective drying.

FIG. 13 depicts an exemplary Inspection Station (300). This station uses a camera and light on each side of the layer pad to inspect for quality defects and undesirable conditions, such as evidence of microbial contamination. In FIG. 13, the plane of light and camera surveillance (311) is shown directed to layer pad (110) progressing through the station. Encoder tracking and photoeye triggers allow for inspection control. Layer pad tracking is additionally accomplished through barcode scanners. Information on the presence or absence of debris, defects, or other indication of contamination is stored so that the layer pad is tagged "reject" as it moves along the system, and data on stacks of layer pads analyzed later by computer (350) storing the data. FIG. 14 shows a top view of the inspection station. Additional capability of the vision system includes both reading and writing barcodes on layer pad as they traverse through the Inspection Station.

FIG. 15 depicts a second VFC and layer pad (110) moving through it. In FIG. 1, the second VFC is shown as (600). Also in FIG. 1 is the flopping station (500), which is the flipping station (400) oriented 90 degrees different in order to flip the layer pad from vertical back to horizontal. Each VFC allows for quick entry and exit ports to add layer pads for testing and clear pads in the case of jams or unwanted conditions.

Figure 16:
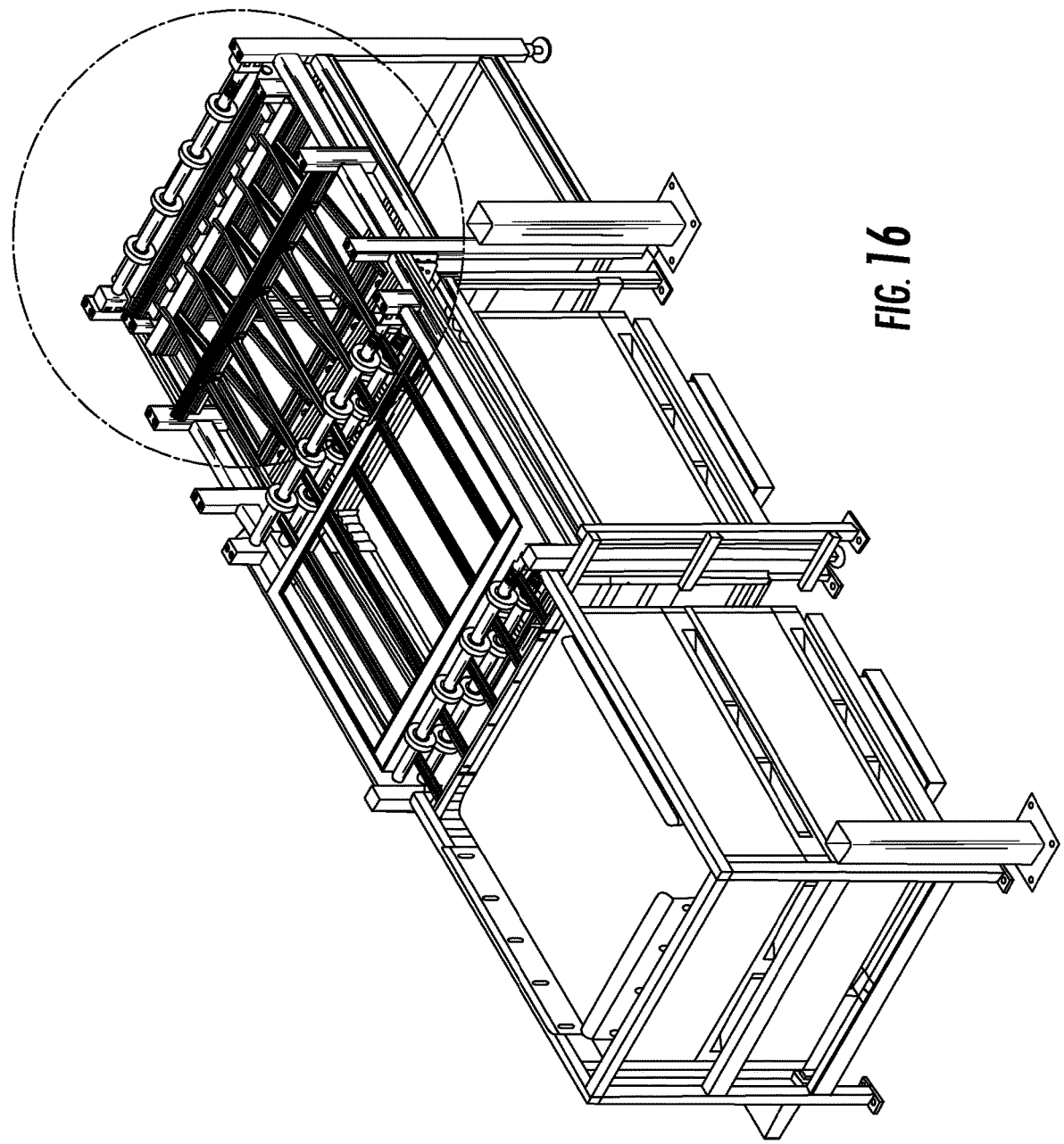
Figure 17:
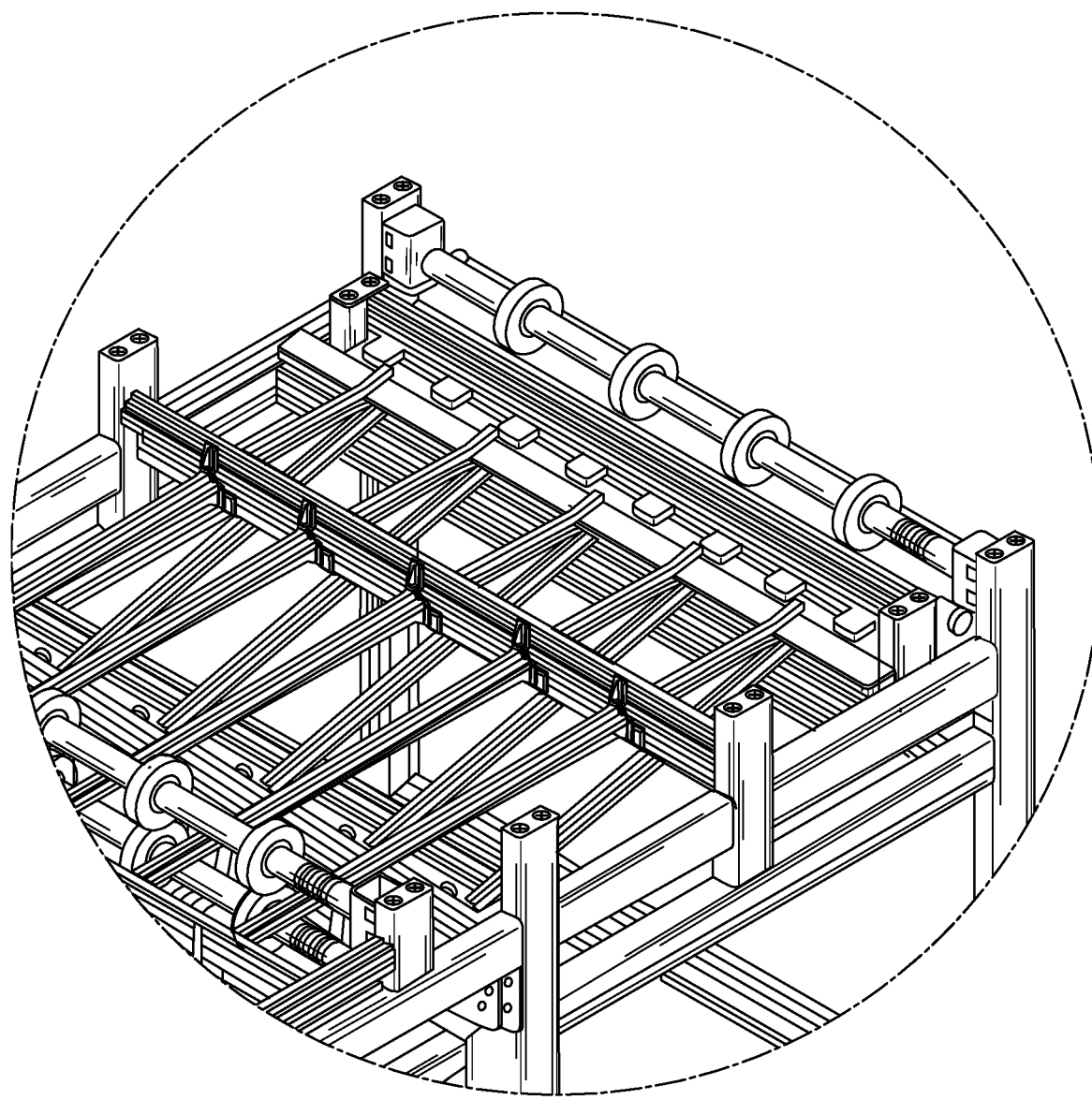

FIGS. 16-18 depict the Sorter/Stacker (800) of FIG. 1. From the data derived from the inspection station, each layer pad is assigned a "reject" or "acceptable" label or tag in the system. Other additional labels can be determined if desired, so that more than just two stacks could be created. The Sorter/Stacker station uses a pivot arm driven by piston (849) to sort between the two sets ("reject" and "acceptable") of layer pads and direct them to the appropriate stack. In FIG. 18B, either level (847) or (846) as shown can be used to direct layer pads to the "reject" stack or the "acceptable" stack. The reject and acceptable stacks align through pneumatic pistons and product guides.

The system will hold the production line when any of the controls for the placement of the layer pad in the system signals a stop or if the steam temperature falls below a minimum or an inspection result failure. Additionally, the system will stop once an "acceptable" or "reject" pallet reaches a certain height. A plurality of photoeye sensors included throughout the system will track pads for location and faults.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate parts between a connection of elements and relative movement between elements. As such, joinder references do not necessarily infer that two elements are directly connected and in fixed relation to each other.

All matter contained in the above description or shown in the accompanying drawings shall be interpreted as illustrative only and not limiting. Changes in detail or structure may be made without departing from the spirit of the invention as defined in the appended claims.

What is claimed is:

1. A system comprising:
  a receiving and loading station having a controlling unit and at least one top roller, wherein the receiving and loading station singulates and inducts a single layer pad from a stack of layer pads comprising flat surfaces, and wherein each single layer pad has a flat surface;
  a flipper station having a first set of flipper station belt rollers at a first flipper station end and a second set of flipper station belt rollers at a second flipper station end, wherein the second set of flipper station belt rollers define a second flipper station plane and the first set of flipper station belt rollers define a first flipper station plane, wherein the first flipper station plane is perpendicular to the second flipper station plane;
  a steam cleaning station having a first set of steam cleaning station belt rollers at a first end of the steam cleaning station and a second set of steam cleaning station belt rollers at a second end of the steam cleaning station, the steam cleaning station further comprising a steam generator that provides steam to at least one flat surface of the single layer pad for sterilization, wherein the steam cleaning station is configured to input the single layer pad through the first set of steam cleaning station belt rollers and output the single layer pad through the second set of steam cleaning station belt rollers;
  an inspection station comprising a camera for inspecting each of the at least one flat surface of the single layer pad;
  a flopper station having a first set of flopper station belt rollers at a first flopper station end and a second set of flopper station belt rollers at a second flopper station end, wherein the second set of flopper station belt rollers define a second flopper station plane and the first set of flopper station belt rollers define a first flopper station plane, wherein the first flopper station plane is perpendicular to the second flopper station plane; and a sorter/stacker station comprising a pivot arm driven by a piston that directs the single layer pad into one or more stacks, wherein the system is configured to sequentially process the single layer pad through the receiving and loading station, the flipper station, the steam cleaning station, the inspection station, the flopper station, and the sorter/stacker station.

2. The system according to claim 1, wherein the steam cleaning station contains at least one set of sealing rollers, the at least one set of sealing rollers substantially sealing at least a portion of the flat surface of the single layer pad during a steam treatment.

3. The system of claim 1, wherein the flipper station is positioned before the inspection station and is configured to rotate the single layer pad from a horizontal position to a vertical position where the flat surface of the single layer pad is perpendicular to the ground.

4. The system of claim 1, wherein the flopper station is positioned after the inspection station and is configured to rotate the single layer pad from a vertical position to a horizontal position where the flat surface of the single layer pad is parallel to the ground.

5. The system according to claim 1, wherein a stack of layer pads of the one or more stacks comprises one or more layer pads stacked in a consistent manner.

6. The system according to claim 1, further comprising a vertical flats conveyor that is capable of controlling a position of a bottom edge of the single layer pad as the single layer pad is moved between one or more stations between the flipper station and the flopper station.

7. The system according to claim 1, wherein the inspection station contains one or more cameras on each side of the flat surface of the single layer pad, and each camera is capable of detecting holes in the single layer pad or differences associated with microbial contamination.

8. The system according to claim 1, wherein the steam cleaning station is designed so that regions of each side of the flat surface of the single layer pad is brought to 160 degrees Fahrenheit during a time the single layer pad traverses the steam cleaning station, whereby the flat surface of the single layer pad is treated to 160 degrees Fahrenheit.

9. The system according to claim 1, wherein the steam cleaning station further comprises a first steam treating unit having a first steam treating unit roller and a second steam treating unit having a second steam treating unit roller.

10. A system comprising:
a flipper station having a first set of flipper station belt rollers at a first flipper station end and a second set of flipper station belt rollers at a second flipper station end, the second set of flipper station belt rollers are oriented 90 degrees different from the first set of flipper station belt rollers, wherein the flipper station is configured to input a single layer pad through the first set of flipper station belt rollers and output the single layer pad through the second set of flipper station belt rollers;
a steam cleaning station having a first set of steam cleaning station belt rollers at a first end of the steam cleaning station and a second set of steam cleaning station belt rollers at a second end of the steam cleaning station, the steam cleaning station further comprising a steam generator that provides steam to at least one side of a flat surface of the single layer pad, wherein the steam cleaning station is configured to input the single layer pad through the first set of steam cleaning station belt rollers and output the single layer pad through the second set of steam cleaning station belt rollers; and
a flopper station having a first set of flopper station belt rollers at a first flopper station end and a second set of flopper station belt rollers at a second flopper station end, the second set of flopper station belt rollers are oriented 90 degrees different from the first set of flopper station belt rollers, wherein the flopper station is configured to input a single layer pad through the first set of flopper station belt rollers and output the single layer pad through the second set of flopper station belt rollers, wherein the system is configured to sequentially flip the single layer pad via the flipper station, steam clean the single layer pad via the steam cleaning station, and flop the single layer pad via the flopper station.

11. The system according to claim 10, further comprising a receiving and loading station having a controlling unit and at least one top roller, wherein the receiving and loading station singulates and inducts the single layer pad from a stack of layer pads comprising flat surfaces such that the flipper station receives the single layer pad, each single layer pad has a flat surface.

12. The system according to claim 11, further comprising an inspection station comprising a camera for inspecting each side of the flat surface of the single layer pad after the single layer pad has been steam cleaned by the steam cleaning station and before the single layer pad is flopped by the flopper station.

13. The system according to claim 12, wherein the inspection station contains one or more cameras on each side of the flat surface of the single layer pad, and each camera is capable of detecting holes in the single layer pad or differences associated with microbial contamination.

14. The system according to claim 12, further comprising a sorter/stacker station comprising a pivot arm driven by a piston that directs the single layer pad into one or more stacks after the single layer pad has been flopped by the flopper station.

15. The system according to claim 10, wherein the steam cleaning station contains at least one set of rollers, the at least one set of rollers substantially sealing at least a portion of the flat surface of the single layer pad during a steam treatment.

16. The system of claim 12, wherein the flipper station is positioned before the inspection station and is configured to rotate the single layer pad from a horizontal position to a vertical position where the flat surface of the single layer pad is perpendicular to the ground.

17. The system of claim 12, wherein the flopper station is positioned after the inspection station and is configured to rotate the single layer pad from a vertical position to a horizontal position where the flat surface of the single layer pad is parallel to the ground.

18. The system according to claim 14, wherein a stack of the one or more stacks comprises one or more layer pads stacked in a consistent manner.

19. The system according to claim 10, further comprising a vertical flats conveyor that is capable of controlling a position of a bottom edge of the single layer pad as the single layer pad is moved between one or more stations between the flipper station and the flopper station.

20. The system according to claim 10, wherein the steam cleaning station is designed so that regions of each side of the flat surface of the single layer pad is brought to 160 degrees Fahrenheit during a time the single layer pad traverses the steam cleaning station, whereby the flat surface of the single layer pad is treated to 160 degrees Fahrenheit.

21. The system according to claim 10, wherein the steam cleaning station further comprises a first steam treating unit having a first steam treating unit roller and a second steam treating unit having a second steam treating unit roller.

\* \* \* \* \*